United States Patent [19]

Muneyuki et al.

[11] Patent Number: 4,912,137
[45] Date of Patent: Mar. 27, 1990

[54] FABRIC INSECTICIDE

[75] Inventors: Ryonosuke Muneyuki; Hiroyuki Kanamaru, both of Tokyo, Japan

[73] Assignee: S. T. Chemical Co., Ltd., Tokyo, Japan

[21] Appl. No.: 217,853

[22] Filed: Jul. 12, 1988

[51] Int. Cl.$^4$ ............................................. A01N 37/00
[52] U.S. Cl. ..................................................... 514/574
[58] Field of Search .......................................... 514/574

[56] References Cited

U.S. PATENT DOCUMENTS 2,852,426  9/1958  Stansbury ............................ 514/574

OTHER PUBLICATIONS

Chemical Abstracts (95)16: 134271j, "Chemical Approach for Sewing. Part 1. Temporary Finishing Agents for Sewing Limp Fabrics", 10/19/81.

*Primary Examiner*—Douglas W. Robinson
*Assistant Examiner*—Raymond J. Henley, III

[57] ABSTRACT

An insecticide which comprises an oxalic ester of the formula:

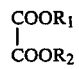

wherein $R_1$ and $R_2$ are, the same or different, each a hydrogen atom or a $C_1$-$C_4$ alkyl group but at least one of them is a $C_1$-$C_4$ alkyl group.

2 Claims, No Drawings

FABRIC INSECTICIDE

The present invention relates to an insecticide for fibrous materials. More specifically, it relates to an insecticide for prevention of fibrous materials such as fabrics and clothes from the damage by insects such as beetles, moths and worms.

Hiterto, there are known naphthalene, camphor, p-dichlorobenzene, etc. as insecticides. However, their lethal activities are not satisfactory. For instance, naphthalene can not prevent the feeding damage of fibrous materials by the larvae of insects, and naphthalene and camphor are weak in lethal activity against the larvae. p-Dichlorobenzene shows higher prevention of feeding damage and stronger lethal activity than naphthalene and camphor but its effect is still not adequate. In addition, the combined use of p-dichlorobenzene with camphor produces stains on fibrous materials and gives damage on plastics enveloping such fibrous materials.

As the results of an extensive study overcoming said drawbacks as seen on conventional fabric insecticides, it has been found that an oxalic ester of the formula:

$$\begin{array}{c} COOR_1 \\ | \\ COOR_2 \end{array} \quad (I)$$

wherein $R_1$ and $R_2$ are, the same or different, each a hydrogen atom or a $C_1$-$C_4$ alkyl group but at least one of them is a $C_1$-$C_4$ alkyl group shows a remarkable insecticidal effect and produces significant prevention of the feeding damage by insects or their larvae. This invention is based on the above finding.

Typical examples of the oxalic ester (I) are as follows:

| Chemical formula | M.P. | Remarks |
| --- | --- | --- |
| $CH_3OOCCOOCH_3$ | 54° C. | sublimating |
| $C_2H_5OOCCOOC_2H_5$ | −40.6° C. (bp. 185.7° C.) | |
| $CH_3OOCCOOC_2H_5$ | — | Acute toxicity (orally, mouse), $LD_{50}$: 2000 mg/kg |
| $C_4H_9OOCCOOC_4H_9$ | 29° C. (bp. 239–240° C.) | |

A typical test example which supports the excellent insecticidal activity of the oxalic ester (I) is set forth below.

A weighed amount (1 g) of each test compound was placed at the bottom of a glass bottle (inner volume, 1 liter) having a cap. Ten larvae of clothes moth (*Tinea pellionella*) and a lump of wool (about 100 mg) were admitted into a stainless wire cage (volume, about 0.08 liter), which was then admitted into the glass bottle. The glass bottle was allowed to stand in a bath of constant temperature and humidity (20° C.; 75% R.H), and observation was made one week and one month thereafter. The averaged results obtained with five experiments carried out at the same time are shown in Table 1.

TABLE 1

| Test compound | After one week | | | After one month | |
| --- | --- | --- | --- | --- | --- |
| | Vaporized amount of test compound (mg) | Damaged weight of wool (mg) | Number of killed larvae | Damaged weight of wool (mg) | Number of killed larvae |
| Dimethyl oxalate | 22 | 2.7 | 8/10 | 3 | 10/10 |
| Diethyl oxalate | 2.4 | 3 | 10/10 | — | — |
| Di-n-butyl oxalate | <0.5 | 30 | 2/10 | 35 | 5/10 |
| None | — | 56.7 | 0/10 | 200 | 0/10 |
| p-Dichlorobenzene | 104 | 4 | 9/10 | 6 | 10/10 |

Judging from the smaller vaporized amounts, dimethyl oxalate, diethyl oxalate and di-n-butyl oxalate may be understood to show a higher insecticidal effect in comparison with p-dichlorobenzene. The damaged weight of wool in their presence is quite small. Thus, they are useful as insecticides.

For the practical use, the oxalic ester (I) of this invention may be applied as such to fibrous materials to be protected from the damage by insects. Alternatively, it may be formulated together with any solid or liquid carrier or diluent (e.g. adamantane, liquid paraffin) into a conventional preparation form (e.g. granules, tablets); the thus formulated preparation is applicable to fibrous materials to be protected.

A practical embodiment of the invention is illustratively shown in the following Example.

EXAMPLE 1

Dimethyl oxalate (20 g) was tabletted by a conventional procedure to make tablets, which had each a weight of 5 g and were lapped with partial air-tight paper. Four tablets thus obtained were placed on a fabric made of wool (about 2 kg) in a container (50 liters) made of wood. After two months, the tablet decreased to 2.5 g at 25° C. and no damage from the larvae set aside was observed on the fabric.

The insecticide of the invention is advantageous in exerting a high insecticidal effect with less toxicity to human beings.

What is claimed is:

1. A method for preventing insect damage to fibrous material, said method comprising maintaining said fibrous material and an oxalic ester which is in a shaped form and is independent of said fibrous material, in a relationship such that vapor from said shaped form contacts the fibrous material, said oxalic ester having the formula:

$$\begin{array}{c} COOR_1 \\ | \\ COOR_2 \end{array}$$

wherein $R_1$ and $R_2$ are the same or different and are selected from the group consisting of a hydrogen atom and a $C_1$-$C_4$ alkyl group, with at least one of $R_1$ and $R_2$ being a $C_1$-$C_4$ alkyl group.

2. The method according to claim 1, wherein the oxalic ester is dimethyl oxalate.

* * * * *